United States Patent [19]

Leonard

[11] Patent Number: 4,820,287

[45] Date of Patent: Apr. 11, 1989

[54] SYRINGE FOR HIGH PRESSURE INJECTION OF FLUID OR PASTE PRODUCTS

[75] Inventor: Henry Leonard, Besançon, France

[73] Assignee: Micro-Mega, Besançon, France

[21] Appl. No.: 30,709

[22] Filed: Mar. 25, 1987

[30] Foreign Application Priority Data

Mar. 27, 1986 [FR] France ............................... 86 04657

[51] Int. Cl.⁴ ............................................. A61M 5/00
[52] U.S. Cl. .................................... 604/209; 604/210; 604/224; 604/135
[58] Field of Search ............................... 604/209–210, 604/224, 135; 222/391

[56] References Cited

U.S. PATENT DOCUMENTS

| | | | |
|---|---|---|---|
| 2,472,116 | 6/1949 | Maynes | 604/224 |
| 2,475,939 | 7/1949 | Applezweig | 604/224 |
| 2,725,877 | 12/1955 | Reiter et al. | 604/224 |
| 3,507,276 | 4/1970 | Burgess | 604/135 |
| 4,377,380 | 3/1983 | Vadas et al. | 222/391 |
| 4,581,022 | 4/1986 | Leonard et al. | 222/391 |
| 4,659,327 | 4/1987 | Bennett et al. | 604/224 |

Primary Examiner—C. Fred Rosenbaum
Assistant Examiner—Colleen Reilly
Attorney, Agent, or Firm—Horst M. Kasper

[57] ABSTRACT

A syringe is provided with a helical spring, which furnishes an upper limit to a pressure employed via a plunger to move a fluid or paste through an opening in a syringe. The plunger is maintained in a low compressing state versus the fluid with the helical spring. A toothed rack is attached to the plunger. The toothed rack is engaged by a ratchet forming part of a lever. The lever is hinged on an axially movable assembly. Actuation of the lever drives the ratchet and therewith toothed rack and plunger forward against the force of the spring. As more force is applied to the plunger the resilient force of the compression spring allows the axially movable assembly to move backward and thus to limit the pressure exerted by the plunger on the fluid. A second ratchet can be provided for preventing a backward motion of the toothed rack while the lever seeks a new point of engagement for the ratchet with the toothed rack. A spring can be employed for assuring simultaneous engagement of first and second ratchet with the toothed rack. The helical spring can be round or rectangular.

22 Claims, 2 Drawing Sheets

SYRINGE FOR HIGH PRESSURE INJECTION OF FLUID OR PASTE PRODUCTS

BACKGROUND OF THE INVENTION

1. Field of the Invention

The invention relates to a syringe for the high pressure injection of fluid or paste products of the type where force is transmitted to a plunger via a lever which acts on a toothed rack incorporated into the plunger.

2. Brief Description of the Background of the Invention Including Prior Art

Syringes for high pressure injection of fluid or pasty products are known from French Patent Application No. 82/18546 where the force exerted by the user is transmitted to the plunger by a toothed rack multiplying force transmission. The syringe is comprised of a case with a forward area suitable for containing the product to be injected and a rear area, sealed at the back but with its forward end open to communicate with the forward area when the two are connected. A needle holding system or an ejector nozzle may be connected to the forward area. A toothed plunger rod is movably mounted in the case and can take any position between "loaded" when it is housed wholly in the rear area, and "injection completed" when it is housed wholly in the forward area, having discharged the product to be injected through either a needle or a nozzle. A forward-angled operating lever pivoting on pivots in the rear area moves a first ratchet, in opposition to a first flexible component, to exert a forward thrust on the toothed rack cut along the side of the plunger when pressure is exerted on the lever. A second ratchet, in concert with a second flexible component, co-operates with the toothed rack to prevent any backward motion. Means acting in opposition to this second elastic component are provided to free the rack from the second ratchet to allow the return of the plunger from "emptied" to the "loaded" position.

A known advantage of this system is the considerable multiplication of the pressure exerted on the lever by the user, which facilitates ejection of the product, normally requiring great effort either because of the fineness of the injection needle or the high viscosity of the paste product. However, the disadvantage exists that the considerable pressure exerted by the plunger on the product may attain a level such that one or another of the system components fails, either the tube containing the liquid bursts or the pivot pin of the lever buckles.

SUMMARY OF THE INVENTION

1. Purposes of the Invention

It is an object of the present invention to provide a high pressure injection syringe having a lever operated plunger with a system limiting the pressure exerted upon the product to be ejected.

These and other objects and advantages of the present invention will become evident from the description which follows.

2. Brief Description of the Invention

The present invention provides a syringe for applications involving pressure generation for moving fluids comprising a syringe casing with a plunger having a head adapted to move inside the syringe casing. A rear area is provided in the casing to the rear of the plunger. An axially mobile assembly movably is disposed in the syringe casing in an area to the rear of the plunger. A calibrated helical compression spring force transmittingly engages the axially mobile assembly. A toothed rack attached to the plunger is engaged by a lever hinged to the axially mobile assembly for limiting a pressure exerted by the plunger head upon the fluid to be ejected by the syringe, such that the calibrated helical compression spring interposed in a kinematic chain converts an angular displacement of the lever of the syringe into an axial displacement of the toothed rack controlling the said plunger, with the calibration setting corresponding to a maximum admissible pressure to be exerted upon the fluid for ejection.

A pivot pin can support the lever on the movable assembly. The calibrated helical spring can be mounted in opposition to the displacement of the axially mobile assembly bearing the pivot pin so that the mobile assembly gives way when a force applied to the lever would generate a force on the fluid or paste to be ejected that is greater than the maximum pressure desired to be exerted thus limiting a forward movement of the said toothed rack when the maximum pressure level is reached.

The axially mobile assembly can comprise a longitudinal shoe. Guides can be formed upon each side of an intermediate section of the syringe casing.

The mobile assembly can comprise a pair of longitudinal shoes sliding on guides formed upon each side of an intermediate section of the syringe casing and interlocked with a block housed in the rear area of the casing such that rearward travel is opposed by the calibrated helical compression spring generating a resistance limited to a maximum admissible pressure.

A screwable rear area of the syringe casing can mesh with an intermediate section of the syringe casing in which the axially mobile assembly slides. The calibrated force of the helical compression spring, which can be of rectangular or circular section, can be adjustable by screwing the rear area of the syringe casing.

A ratchet can be attached to the lever to engage the toothed rack and provide support to the toothed rack on the rear side in order to assure a forward motion of the plunger. A hinge axis can support the ratchet tiltably around a hinge support disposed at the lever. A button can be manually actuated for moving the lever to disengage the ratchet from the toothed rack. A second ratchet attached to the button can engage the toothed rack for locking the toothed rack in position during the operation of the lever. A spring can simultaneously maintain the first ratchet and the second ratchet in an engaged position with the toothed rack and can provide a force opposed to actuation of the button. A leaf spring can be disposed between the first ratchet and a hinge axis on the lever for the ratchet in order to provide a resilient force in horizontal direction between the plunger and the axially mobile assembly.

The axially movable assembly can comprise a pair of longitudinal shoes free to slide longitudinally along guide rails which can be mounted to the syringe casing over the whole length of two diametrically opposed generating lines.

An inner thread can be disposed in a rear area of the syringe casing to engage a threaded rod having an outer thread where the threaded rod can be turned in the casing to adjust the tension of the helical compression spring. A slotted recess can be provided in the end of the threaded rod to be accessible from outside of the casing for adjusting the position of the threaded rod for tensioning the helical compression spring.

Another embodiment of the present invention provides a syringe for applications involving pressure generation for moving fluids which comprises a syringe casing with a plunger having a head and adapted to move inside the syringe casing and having a rear area relative to its position in the casing. An axially mobile assembly is movably disposed in the syringe casing in an area to the rear of the plunger, and a toothed rack is attached to the plunger. An operating lever hinged to the axially mobile assembly engages the toothed rack with a leaf spring interposed between the operating lever and the toothed rack, for limiting a pressure exerted by the plunger head upon the fluid to be ejected by the syringe, such that the leaf spring buckles when the force exerted by the lever exceeds a maximum admissible pressure.

Another aspect of the present invention provides a method for pressure stabilization in a syringe for fluid output. A syringe casing containing a plunger is employed where a lever is hinged on an axially slidable assembly disposed in the casing. A toothed rack attached to the plunger is engaged by a ratchet supported by the lever. The pressure exerted by the plunger onto the fluid is limited by allowing the lever hinge to move backward against the force of a compression spring upon exceeding of a limiting force. The plunger is actuated against the force of the spring by the lever operating the ratchet engaging the toothed rack for advancing the plunger and thereby compressing the fluid.

A backward motion of the toothed rack can be prevented by a second ratchet locking the toothed rack in position against the reaction force of the fluid or paste to be ejected. The toothed rack can be released by actuating a button, which moves the lever with the first ratchet and the second ratchet in a disengaged position relative to the toothed rack. The lever and the button can be tensioned with a spring such that the first ratchet and the second ratchet are both maintained in engagement with the toothed rack.

The present invention provides a syringe for high pressure injection of fluid or paste products where force is transmitted to a plunger by pressure on a lever which acts via a ratchet on a toothed rack comprising a part of the plunger. In the prior art the lever is mounted on fixed pivot pins. The present invention provides a system for limiting the pressure exerted on the product which comprises mounting the lever pivot pin not to the syringe casing but to an axially mobile helicoidal unit of the syringe casing in opposition to a compressible spring calibrated to the maximum admissible pressure to be exerted on the product to be injected.

According to a preferred construction configuration, the pivot mounting unit consists of a pair of longitudinal shoes free to slide along guides formed on each side of an intermediate section of the syringe and interlocked with a bloc housed in the rear area of the syringe casing such that the rearward movement of the pivot pin mounting unit is braked by a spring exerting a maximum load which is at most equal to the maximum admissible pressure on the plunger.

The spring is preferably a compressible helical wire spring of either round or square section positioned behind the bloc. Cost savings may be obtained by replacement with a leaf spring bearing on the toothed rack and the lever and bending under a load at most equal to that of the maximum acceptable pressure on the plunger.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

In the accompanying drawing, in which is shown a possible embodiment of the present invention.

DESCRIPTION OF INVENTION AND PREFERRED EMBODIMENT

Figure 1:
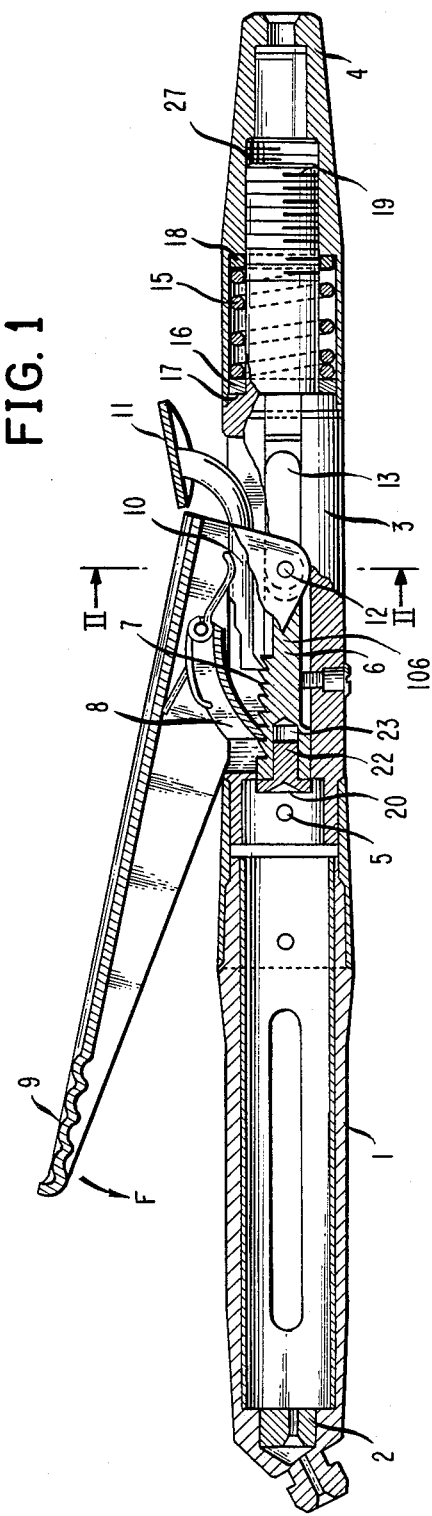
FIG. 1 is a schematic view of an axial section of the syringe in accordance with the present invention.
Figure 2:
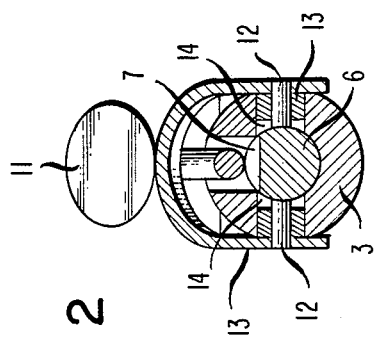
FIG. 2 is a cross-sectional view along section II—II of FIG. 1.

According to FIG. 1, the forward area 1 of the syringe casing is fitted with a needle holder 2 in the frontal section. The rear area of the syringe casing, in accordance with the present invention, is sub-divided into two sections, an intermediate area 3 and a rear area 4. The intermediate section 3 is connected to the forward area 1 by a bayonet system indicated as 5. The rear area 4 is adapted to the intermediate section 3 by threading, indicated as 27, the function of which will be explained in greater detail below.

Pressure is exerted on the product to be injected by a plunger 6, forming part of a mobile assembly 106 with a toothed rack 7 disposed into its upper side. The toothed rack 7 respectively engages a first ratchet 8, activated by the operating lever 9, and a second ratchet 10 which can be released by pressing on button 11 to permit rearward return of the toothed rack. The teeth of the toothed rack are formed such that they can maintain the plunger pressing against a fluid while engaged with a ratchet.

In accordance with the present invention, the pivots 12 of lever 9 are not mounted to a fixed part of the casing but to a pair of shoes 13 free to slide longitudinally on guide rails 14 formed over the whole length of two diametrically opposed rods disposed along the intermediate casing 3. The pair of shoes can move independently from the toothed rack. Thus the lever sets up a tension force between the toothed rack and the pair of shoes. Since the pair of shoes are resiliently supported by a compression spring, which is in particular set for yielding after a certain maximum pressure has been attained, the pressure exerted on the plunger can be limited to a desired value determined by parameters including the calibration of the compression spring.

The shoes 13 bear on a pressure compensating system within the rear area 4 of the syringe casing. The pressure compensating system comprises a helical spring 15, housed between a thrust washer 16, which engages a shoulder 17 of intermediate section 3 of the syringe, casing, and a further ridge 18 disposed on the interior of the casing of rear section 4 and facing in the opposite direction to shoulder 17. The shoulder 17 can make angle of from about 90 to 100 degrees with respect to the surface of the casing of intermediate section 3. The ridge 18 can be disposed along from about two thirds to one half of the rearmost section of the casing of rear area 4. The longitudinal surface of the ridge 18 is threaded with threading 27.

The intermediate section 3 is extended into area 4 by a threaded rod 19 that passes through the thrust washer 16 and the helical coil 15 and meshes with the threading 27 disposed on the interior of the casing of the rear area 4 in the area of the ridge 18. The rod 19 extends rearward from the shoulder 17 of the intermediate section 3. The threading of the rod 19 and the threading 27 can be disposed at an angle of from about 45 to 55 degrees relative to the longitudinal axis of the rod 19, which coincides with the longitudinal axis of the rear section 4. By varying the distance that the intermediate section 3 is screwed into the rear area 4, the compression of the helical spring 15 between the ridge 18 of rear area 4 and the thrust washer 16 engaged by the shoulder 17 of intermediate area 3 may be reduced or increased to obtain the required load. For a helical spring of given strength, the penetration distance of intermediate section 3 into rear section 4 can be calibrated to give specific settings of the maximum pressure desired.

In operation, when the user actuates lever 9 in the direction of arrow F, ratchet 8 engages a tooth on rack 7 causing the rack and consequently the plunger head to advance by the length of one tooth with each pressing of the lever 9.

To ease visualization, area 1 is presented without a tube, normally containing liquid, and without a needle fitted to the needle holder 2. Area 1 may be produced differently is a pastry substance is to be ejected through a nozzle mounted instead of needle holder 2.

In either case, prior to the present invention the user was faced with a similar problem in that after pressing lever 9 a certain number of times, the plunger head 20 attains maximum compression and the elastic plug of the liquid capsule or the paste product meets ever increasing resistance. Because of the great multiplication of force F, with a fixed pivot the lever 9 may still be manipulated even though the resulting stress exceeds the strength of the liquid containing tube or even that of the mechanical components of the syringe, paticularly the pivot pins of lever 9. This could result in a burst capsule or breakage of one of the mechanical components, for example a fixed pivot. In the present invention, with the helical spring 15 calibrated to maximum admissible pressure by the distance intermediate section 3 is screwed into rear section 4, continued manipulation of lever 9 will tend to compress the helical spring 15, allowing pivot 12 mounted on the movable guideshoes 13 to move to the rear and thus free the corresponding tooth of rack 7. The load exerted upon the product and/or the mechanical components of the syringe is thereby limited to the desired maximum admissible value to avoid breakage since any overload is borne by the calibrated helical spring 15. Consequently, any risk of syringe breakage is eliminated, even in the event of inexpert handling.

In accordance with a further practical application of the pressure compensating system, lever 9 may be actuated in rapid succession to instantaneously load helical spring 15 before the plunger head 20 has had time to exert excessive pressure. Plunger 22 can move in the cylinder bore 23. Lever 9 is then released immediately so that helical spring 15 progressively exerts pressure upon the plunger 6, the head of which consequently ejects the product for injection very slowly and gradually without risk of breaking either the capsule or the mechanical components of the syringe.

Calibration of the said helical spring 15 enables the system for pressure limitation to be adapted to the nature of the product for injection, namely to the fineness of the needle or to the viscosity of the paste product to be ejected.

In accordance with another embodiment of the pressure compensation system, the helical spring 15 may be replaced by a simple leaf spring, where such simple leaf spring bears upon both the rack 7 and lever 9 so that when ratchet 8 encounters excessive resistance from a tooth of rack 7 the spring bends, thus preventing the force exerted on lever 9 from being transmitted to the rack and consequently to plunger head 20.

Figure 3:
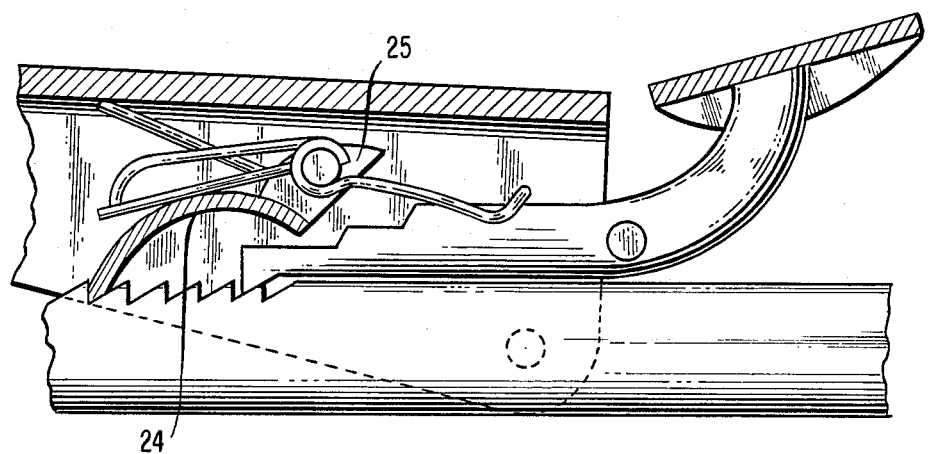
FIG. 3 is a view of an enlarged part of the section of FIG. 1 in the area of the toothed rack.

FIG. 3 shows an enlarged section of the area near button and lever hinge. A leaf spring 24 is shown located at the lever and having one end provided as a ratchet. The hinge for the lever is provided near 25. A spring is further provided to maintain the leaf spring 24 in engaged position. A further spring can be seen acting between the lever and the button for maintaining both the ratchet end of the button actuator and the ratchet end of the leaf spring engaged with the toothed rack. The hingepoint of the lever is within an inner fifth part of the toothed rack.

Figure 4:
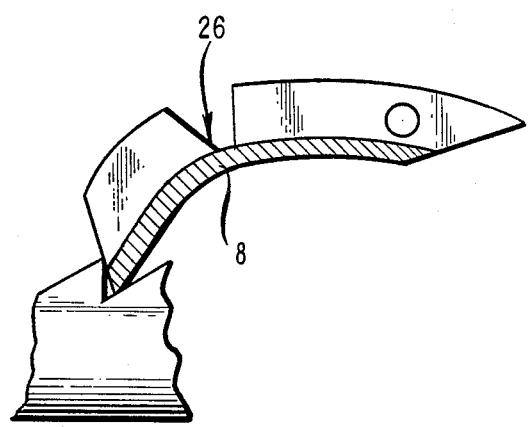
FIG. 4 is a view of an enlarged part of FIG. 1 illustrating engagement of a rachet with the toothed rack.

FIG. 4 is a detail view of a preferred embodiment in the area of engagement of ratchet and toothed gear. A spring supporting the ratchet 8 is constructed so as to yield upon attainment of a certain pressurizing force. A cutout is provided in a section 26 of the leaf spring and this allows the leaf spring to provide for a quasi release of the toothed gear upon attainment of a desired force.

It will be understood that each of the elements described above, or two or more together, may also find a useful application in other types of force limiting configurations differing from the types described above.

While the invention has been illustrated and described as embodied in the context of a syringe for high pressure injection of fluid or paste products, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A syringe for applications involving pressure generation for moving fluids comprising
   a syringe casing;
   a plunger having a head, adapted to move inside the syringe casing and having a rear area relative to its position in the casing;
   an axially mobile assembly movably disposed in the syringe casing in an area to the rear of the plunger;
   a calibrated helical compression spring engaging the axially mobile assembly and the compression spring transmittingly forcing the assembly into motion;
   a toothed rack attached to the plunger;
   a lever pivoted to the axially mobile assembly and engaging the toothed rack for limiting a pressure exerted by the plunger head upon the fluid to be ejected by the syringe, such that the calibrated helical compression spring interposed in a kinematic chain converts an angular displacement of the lever of the syringe into an axial displacement of the toothed rack controlling the said plunger, with the calibration setting corresponding to a maximum admissible pressure to be exerted upon the fluid for ejection;

a ratchet attached to the lever for engaging the toothed rack and for providing support to the toothed rack on the rear side in order to assure a forward motion of the plunger;

a button means for manual actuation for moving the lever to disengage the ratchet from the toothed rack.

2. The syringe for applications involving pressure generation for moving fluids according to claim 1 further comprising a pivot pin supporting the lever on said movable assembly where the said calibrated helical spring is mounted in opposition to the displacement of the axially mobile assembly bearing the pivot pin of said lever so that the mobile assembly gives way depending on a force applied to the lever for limiting a forward movement of the said toothed rack when said maximum pressure level is reached.

3. The syringe for applications involving pressure generation for moving fluids according to claim 1 wherein the axially mobile assembly comprises a longitudinal shoe.

4. The syringe for applications involving pressure generation for moving fluids according to claim 1 further comprising guides formed upon each side of an intermediate section of the syringe casing.

5. The syringe for applications involving pressure generation for moving fluids according to claim 1 further comprising guides formed upon each side of an intermediate section of the syringe casing wherein the said mobile assembly comprises a pair of longitudinal shoes sliding on said guides formed upon each side of an intermediate section of the syringe casing with rearward travel being opposed by the calibrated helical compression spring generating a resistance limited to a maximum admissible pressure.

6. The syringe for applications involving pressure generation for moving fluids according to claim 1 further comprising a screwable rear area of the syringe casing meshing with an intermediate section of the syringe casing, in which the said axially mobile assembly slides; and wherein the helical compression spring is of rectangular section, and where the calibrated force of the compression spring is adjustable by screwing the rear area of the syringe casing.

7. The syringe for applications involving pressure generation for moving fluids according to claim 1 further comprising a screwable rear area of the syringe casing meshing with an intermediate section of the syringe casing, in which the said axially mobile assembly slides; and wherein the helical compression springe is of circular section, and where the calibrated force of the compression spring is adjustable by screwing the rear area of the syringe casing.

8. The syringe for applications involving pressure generation for moving fluids according to claim 1 further comprising a pivot axis for supporting the ratchet tiltable around a pivot support disposed at the lever.

9. The syringe for applications involving pressure generation for moving fluids according to claim 1 further comprising a second ratchet engaging the toothed rack and attached to the button means for locking the toothed rack in position during the operation of the lever.

10. The syringe for applications involving pressure generation for moving fluids according to claim 9 further comprising a spring for simultaneously maintaining the first ratchet and the second ratchet in an engaged position with the toothed rack and for providing a force opposed to actuation of the button means.

11. The syringe for applications involving pressure generation for moving fluids according to claim 1 further comprising a leaf spring disposed between the ratchet and a pivot axis on the lever for the ratchet to provide a resilient force in horizontal direction between plunger and axially mobile assembly.

12. The syringe for applications involving pressure generation for moving fluids according to claim 1 further comprising guide rails mounted to the syringe casing over the whole length of two diametrically opposed generating lines; and wherein the axially movable assembly comprises a pair of longitudinal shoes free to slide longitudinally along the guide rails.

13. A syringe for applications involving pressure generation for moving fluids comprising a syringe casing;

a plunger having a head, adapted to move inside the syringe casing and having a rear area relative to its position in the casing;

an axially mobile assembly movably disposed in the syringe casing in an area to the rear of the plunger;

a calibrated helical compression spring engaging the axially mobile assembly and the compression spring transmittingly forcing the assembly into motion;

a toothed rack attached to the plunger;

a lever hinged to the axially mobile assembly and engaging the toothed rack for limiting a pressure exerted by the plunger head upon the fluid to be ejected by the syringe, such that the calibrated helical compression spring interposed in a kinematic chain converts an angular displacement of the lever of the syringe into an axial displacement of the toothed rack controlling the said plunger, with the calibration setting corresponding to a maximum admissible pressure to be exerted upon the fluid for ejection;

an inner thread disposed in a rear area of the syringe casing;

a threaded rod having an outer thread engaging the inner thread, where the threaded rod can be turned in the casing for adjusting a tension of the helical compression spring.

14. The syringe for applications involving pressure generation for moving fluids according to claim 13 further comprising
   a slotted recess in the end of the threaded rod accessible from outside of the casing for adjusting the position of the threaded rod for tensioning the helical compression spring.

15. A syringe for applications involving pressure generation for moving fluids comprising
   a syringe casing;
   a plunger having a head, adapted to move inside the syringe casing and having a rear area relative to its position in the casing;
   an axially mobile assembly movably disposed in the syringe casing in an area of the rear of the plunger;
   a toothed rack attached to the plunger;
   an operating lever pivoted to the axially mobile assembly and engaging the toothed rack;
   a leaf spring interposed between the operating lever and the toothed rack, for limiting a pressure exerted by the plunger head upon the fluid to be ejected by the syringe, such that the leaf spring buckles when the force exerted by the lever exceeds a maximum admissible pressure;
   a ratchet attached to the lever for engaging the toothed rack and for providing support to the toothed rack on the rear side in order to assure a forward motion of the plunger;
   a button means for manual actuation for moving the lever to disengage the ratchet from the toothed rack.

16. A method for pressure stabilization in a syringe for fluid output comprising
   employing a syringe casing containing a plunger;
   pivoting a lever on an axially slidable assembly disposed in the casing;
   attaching a toothed rack to the plunger;
   engaging the toothed rack with a ratchet supported by the lever;
   limiting the power exerted by the plunger onto the fluid by allowing the pivoted lever to move backward against the force of a compression spring upon exceeding of a limiting force;
   actuating the toothed rack against the force of the spring with the lever operating the ratchet engaging the toothed rack for advancing the plunger and thereby compressing the fluid;
   manually actuating a button for means moving the lever to disengage the ratchet from the toothed rack.

17. The method for pressure stabilization in a syringe for fluid output according to claim 16 further comprising preventing a backward motion of the toothed rach with a second ratchet locking the toothed rack in position against the reaction force of the fluid output.

18. The method for pressure stabilization in a syringe for fluid output according to claim 16 further comprising
   releasing the toothed rack by actuating a button means which moves the lever with the first ratchet and the second ratchet in a disengaged position relative to the toothed rack.

19. The method for pressure stabilization in a syringe for fluid output according to claim 17 further comprising
   tensioning the lever and the button means with a spring such that the first ratchet and the second ratchet are both maintained in engagement with the toothed rack.

20. The method for pressure stabilization in a syringe for fluid output according to claim 16 further comprising
   turning a threaded rod in the casing and thereby adjusting a tension of the helical compression spring, wherein
   an inner thread is disposed in a rear area of the syringe casing and wherein the threaded rod has an outer thread engaging the inner thread.

21. The method for pressure stabilization in a syringe for fluid output according to claim 20 further comprising
   adjusting the position of the threaded rod for tensioning the helical compression spring by employing a slotted recess in the end of the threaded rod accessible from outside of the casing.

22. The syringe for applications involving pressure generation for moving fluids according to claim 1 further comprising
   an inner thread disposed in a rear area of the syringe casing;
   a threaded rod having an outer thread engaging the inner thread, where the threaded rod can be turned in the casing for adjusting a tension of the helical compression spring. a slotted recess in the end of the threaded rod accessible from outside of the casing for adjusting the position of the threaded rod for tensioning the helical compression spring.

* * * * *